United States Patent [19]
Sagstetter et al.

[11] Patent Number: 5,086,922
[45] Date of Patent: Feb. 11, 1992

[54] DISPOSAL FOR NEEDLES AND SYRINGES

[75] Inventors: William E. Sagstetter, Denver; John E. Cooke, Lakewood, both of Colo.

[73] Assignee: Medical Safety Products, Inc., Denver, Colo.

[21] Appl. No.: 536,708

[22] Filed: Jun. 12, 1990

[51] Int. Cl.$^5$ .................... B65D 85/24; B65D 83/10; A61M 5/32
[52] U.S. Cl. ..................................... 206/366; 604/198
[58] Field of Search ............... 206/366, 365; 604/192, 604/198

[56] References Cited

U.S. PATENT DOCUMENTS

| | | | |
|---|---|---|---|
| 4,375,849 | 3/1983 | Hamifl | 206/366 |
| 4,466,538 | 8/1984 | Gianni | 206/366 |
| 4,494,652 | 1/1985 | Nelson et al. | 206/366 |
| 4,667,821 | 5/1987 | Shillington | 206/366 |
| 4,738,362 | 4/1988 | Barns et al. | 206/366 |
| 4,798,587 | 1/1989 | Willoughby | 604/110 |
| 4,801,013 | 1/1989 | Bruno | 206/366 |
| 4,802,579 | 2/1989 | Hall et al. | 206/366 |
| 4,807,344 | 2/1989 | Kelson et al. | 29/240 |
| 4,917,243 | 4/1990 | Abrams et al. | 206/365 |
| 4,923,447 | 5/1990 | Morgan | 604/198 |
| 4,986,811 | 1/1991 | Thead et al. | 604/219 |
| 4,995,871 | 2/1991 | Sasaki et al. | 604/219 |

FOREIGN PATENT DOCUMENTS

2624023  6/1989  France ................ 604/198

Primary Examiner—William I. Price
Attorney, Agent, or Firm—Cahill, Sutton & Thomas

[57] ABSTRACT

A receptacle includes a first recess for receiving the anterior end of the barrel of a conventional double ended needle blood collection tube holder to stabilize the holder during threaded disengagement of the needle. A post disposed within the recess includes a slot for receiving a rib of the double ended needle hub to prevent rotation of the hub while the holder is rotated to unthread the hub. Upon threaded disengagement, the needle drops into the receptacle, which drop may be augmented by a leaf spring. A second recess in the receptacle receives the collar of a guard supporting a translatable blood collection tube holder, which holder threadedly engages the hub of a double ended needle. A post within the recess can extend within the collar to engage with a slot a rib of the hub to prevent rotation of the double ended needle upon rotation of the guard to threadedly disengage the hub from the holder. Upon threaded disengagement, the double ended needle drops into the receptacle, which drop may be augmented by a leaf spring.

45 Claims, 4 Drawing Sheets

DISPOSAL FOR NEEDLES AND SYRINGES

BACKGROUND OF THE INVENTION

1. Field of the Invention

The present invention relates to disposals and, more particularly, to disposals for needles and related devices.

2. Description of the Prior Art

To obtain a blood sample for diagnostic purposes, blood is drawn into an evacuated blood collection tube through a double ended needle. The needle includes a hub, an anterior needle for tissue penetration into a blood vessel and a posterior needle having an exterior elastomeric valve. The posterior end of the needle is penetrably inserted within a barrel having female threads for threadedly engaging the hub to retain the double ended needle positionally fixed with respect to the barrel. The proximal end of the barrel is open to receive an evacuated blood collection tube having a stopper for penetrably receiving the posterior needle. Upon venipuncture, blood will flow through the anterior needle and the posterior needle into the collection tube. Upon removal of the collection tube, the elastomeric valve recovers the posterior needle to prevent spontaneous blood flow from the needle. A phlebotomist can then insert a second or more blood collection tubes into the barrel to receive additional blood samples.

Upon completion of the venipuncture procedure, the anterior needle is withdrawn from the patient. While the barrel is often reused, the double ended needle must be safely removed from the barrel without causing needle stick and while avoiding contact with any residual body fluids of the patient to prevent transmission of infectious disease. Typically, a conventional biohazard receptacle for needles is provided with a lid having various shaped slots to engage the needle hub. To dispose of a used needle, the phlebotomist must carefully place the exposed needle hub into the slot, grip and rotate the barrel to unthread the needle and cause the disengaged needle to drop completely through the slot into the underlying container. Since the barrels are often opaque, it is difficult to know when the double ended needle has become completely threadedly disengaged from the barrel. A further danger arises from the upstanding exposed posterior needle until the hub has become sufficiently disengaged from the slot to permit the needle to drop into the receptacle. Aside from hub engaging slots, other devices have been developed including the use of fixed and moveable jaws to engage the needle hub. Mechanized devices for unthreading a double ended needle are also known.

A recently available reusable safety blood collection device includes a holder for engaging the double ended needle, which holder is translatable within a guard to fully enclose and shield both the anterior and posterior needles of the double ended needle. The guard includes an anterior collar for shielding the end of the anterior needle upon retraction of the holder and for supporting therewithin the hub engaging boss of the holder during use. Known syringe disposal devices are not well suited for receiving and disposing needles of such devices since the hub of the double ended needle is shielded by the collar and is not accessible for gripping by the opposed edges of a slot, jaws or the like.

SUMMARY OF THE INVENTION

A post mounted within a receptacle includes a slot for receiving a rib of a conventional double ended needle hub to prevent rotation of the hub upon engagement of the rib. A sloping upper surface of the post encourages downward sliding movement of the needle into the receptacle upon threaded disengagement of the hub. A further post includes an encircling annular slot for receiving the collar of a guard having an enclosed double ended needle supporting holder to permit insertion of a hub rib into a slot of the post. Rotation of the guard with commensurate rotation of the enclosed holder will threadedly disengage the double ended needle from the holder whereafter the needle will drop into the receptacle. To encourage drop of the double ended needle, a vertical side mounted leaf spring may be incorporated, which leaf spring includes a lip for preventing upward withdrawal of the double ended needle. In a variant, the hub engaging and supporting post assembly along with a downwardly directed chute for guiding a double ended needle into a receptacle may be of modular construction attachable to an aperture of any container.

It is therefore a primary object of the present invention to provide apparatus for receiving and disengaging a double ended needle from a blood collection tube holder on completion of a venipuncture procedure.

Another object of the present invention is to provide a slotted post for threadedly disengaging a double ended needle from a blood collection tube holder.

Still another object of the present invention is to provide a slotted post for engaging the hub of a double ended needle to permit unthreading the needle from a blood collection tube holder in combination with a leaf spring to encourage dropping of the needle into an underlying receptacle.

Yet another object of the present invention is to provide an annular slot for receiving a collar of a blood collection tube holder supporting guard, which collar is concentric with a post for receiving a rib of a double ended needle hub threadedly engaged with the holder.

A further object of the present invention is to provide a receptacle mounted post for engaging a rib of a double ended needle hub to permit threaded disengagement of the hub from a supporting blood collection tube holder and to encourage drop of the needle into the post supporting receptacle.

A still further object of the present invention is to provide a method for unthreading a used double ended needle prior to disposal.

A yet further object of the present invention is to provide a method for converting any receptacle to a disposal unit for double ended needles.

A yet further object of the present invention is to provide apparatus and method for safely disposing a double ended needle from a blood collection holder while shielding a clinician from exposure to each end of the needle.

A yet further object of the present invention is to provide a transparent disposal for receiving a double ended needle from a transparent blood collection tube holder to permit visual inspection of the separation an disposal of the needle.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which.

DESCRIPTION OF THE PREFERRED EMBODIMENT

Receptacles for used blood collection tube holders with double ended needles of the type associated with venipuncture procedures have been in existence for a period of years. Such receptacles tend to reduce the likelihood of needle stick and spread of infectious diseases resulting from contact with the needles and body fluids disposed upon and within the needles. When blood collection tube holders used with the needles are not to be disposed, various problems arise in attempting to separate the double ended needle from the holder without requiring a phlebotomist to touch the needle. A number of devices for this purpose have been developed but each suffers from actual or potential problems which preclude repetitive fail safe operation.

Figure 1:
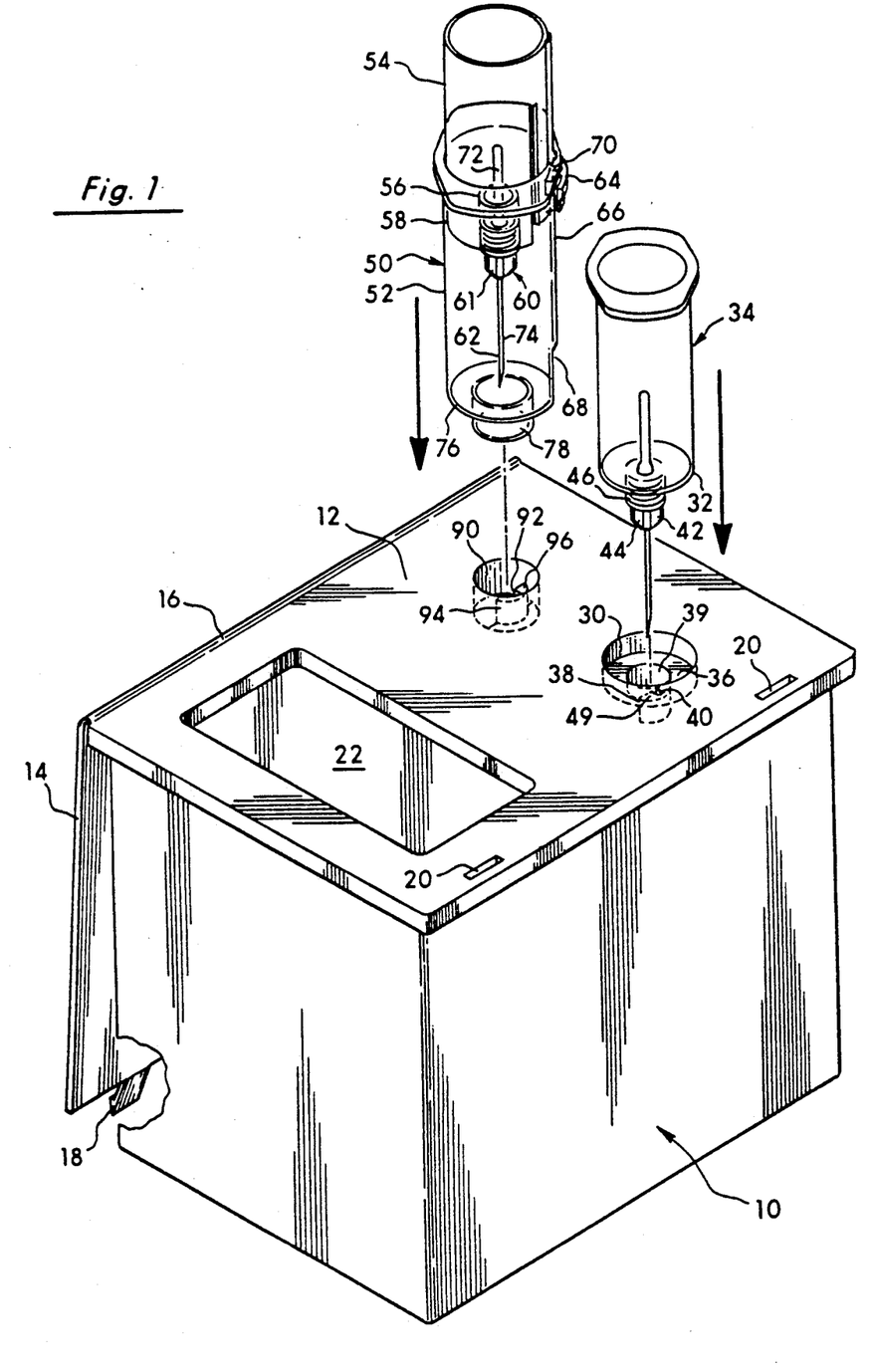
FIG. 1 is an isometric view of a container supporting posts for engaging the hubs of double ended needles threadedly engaged with different types of blood collection tube holders.

Referring to FIG. 1, there is illustrated a receptacle 10 for receiving and housing used double ended needles. The receptacle includes a top surface 12 and a cover 14. The cover may be hinged along hinge line 16. Prongs, such as prong 18 may extend from cover 14 for locking engagement with slots, such as slots 20 formed in top surface 12. An opening 22 may be formed in the top surface to permit insertion into the receptacle of various items for disposal.

Figure 2:
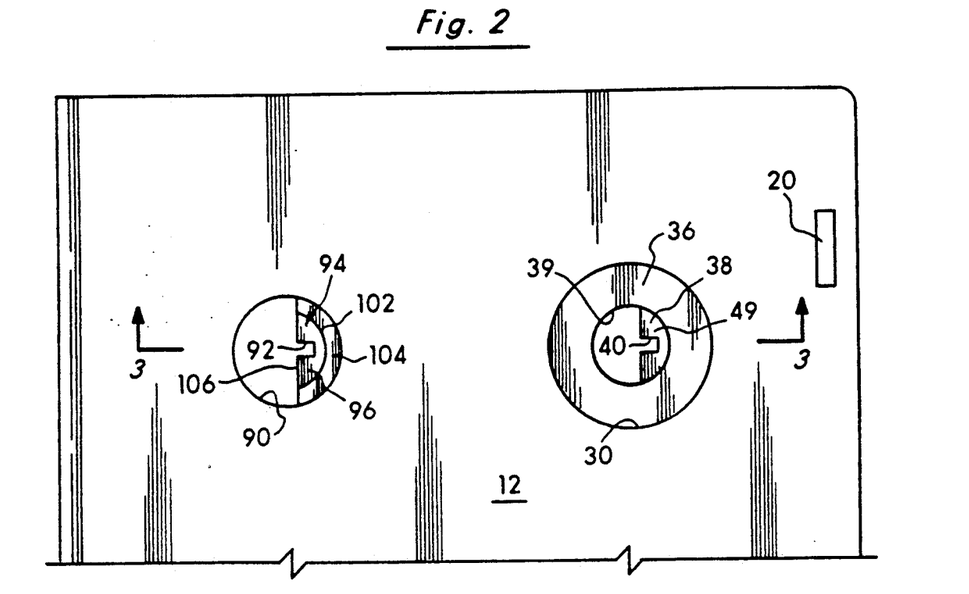
FIG. 2 is a partial top view of two types of post assemblies mounted in a container for receiving used doubled needles.
Figure 3:
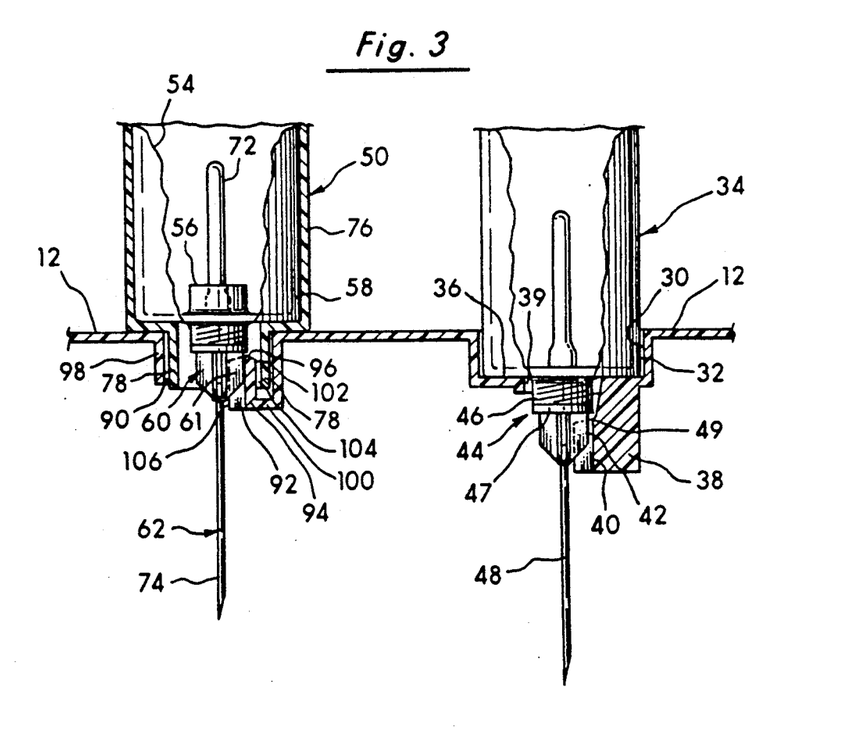
FIG. 3 is a partial sectional view illustrating the relationships between needle hub engaging devices and the respective types of blood collection tube holders.

Referring jointly to FIGS. 1, 2 and 3, a circular recess 30 is formed in top surface 12 to receive and nestingly support cylindrical anterior end 32 of a conventional blood collection tube holder 34. An apertured supporting surface 36, which may be partially or completely annular, is disposed at the bottom end of recess 30 to support anterior end 32 of the blood collection tube holder. A post 38, generally centrally oriented within recess 30, includes a slot 40 for receiving a rib 42 formed in hub 44 of a conventional double ended needle threadedly engaged with boss 46 formed in anterior end 32 of the blood collection tube holder.

To eliminate the possibility of needle stick by phlebotomists during a conventional venipuncture procedure, a more complex blood collection tube holder device 50 has been developed. This device includes a barrel 52 for receiving and supporting a holder 54. The holder includes a boss 56 disposed at anterior end 58 for threadedly engaging hub 60 of a conventional double ended needle 62. A spring loaded tab 64 extends from anterior end 58 of holder 54 for penetrable engagement with and translation along a slot 66 formed longitudinally in barrel 52. Preferably, the slot includes laterally expanded anterior segment 68 and posterior segment 70 for lockingly receiving the tab to retain holder 54 locked in the anterior or posterior position. The axial length of holder 54 is sufficient to fully enclose posterior needle 72 to prevent inadvertent contact with the needle. Upon translation of holder 54 to its posterior position, anterior needle 74 is enclosed within the anterior portion of barrel 52. Anterior end 76 of barrel 52 includes a collar 78 for accommodating penetration therethrough of anterior needle 74 and at least a portion of hub 60 of double ended needle 62. Upon retraction of holder 54 to its posterior position, the end of anterior needle 74 may be located within the confines of collar 78.

To accommodate disengagement of double ended needle 62 from holder 54 on completion of a venipuncture procedure, receptacle 10 may be used. A cylindrical passageway 90 is sized and configured to receive and guide collar 78 through top surface 12 of the receptacle. The passageway also serves the function of stabilizing device 50 during the process of unthreading double ended needle 62 from holder 54. After placement of collar 78 within passageway 90, tab 64 is translated along slot 66 to position hub 60 within collar 78. Simultaneously, a rib 61 of the hub will slidingly engage slot 92 disposed in post 94 located within passageway 90. The size and orientation of post 94 permits the post to extend into collar 78 of device 50 to accommodate engagement with hub 60.

To disengage the double ended needle from blood collection tube holder 34, the holder is inserted into recess 30, guiding the anterior needle 48 through aperture 39 downwardly into adjacent slot 40 until rib 42 of hub 44 slidingly engages the slot. In this position, anterior end 34 of the holder will rest upon and be supported by supporting surface 36. Upon counterclockwise rotation of the holder, commensurate rotation of hub 44 will be precluded by interference between rib 42 and slot 40, resulting in unthreading of the hub from the holder. Upon subsequent raising of the holder out of the recess, the hub, will slide downwardly into the receptacle through the space between post 38 and supporting surface 36. Such downward sliding movement is encouraged if top surface 49 of the post is canted downwardly toward slot 40.

To separate double ended needle 62 from holder 54 of device 50, collar 78 is inserted within passageway 90 until anterior end 76 of barrel 52 rests upon top surface 12 of receptacle 10. Thereafter, tab 64 is brought out of detent or expanded segment 70 and translated along passageway 66 until rib 61 of hub 60 engages slot 92 in post 94. Subsequent counterclockwise rotation of barrel 52 will result in commensurate rotation of holder 54 due to interference therebetween provided by tab 64 and slot 66 or further detent or expanded segment 68. The counterclockwise movement will unthread hub 60 from boss 56. Prior to or upon lifting of device 50, disengaged double ended needle 62 will drop through the space intermediate post 94 and passageway 90. Downward sliding movement of the double ended needle will be enhanced if top surface 96 of post 94 cants downwardly toward the slot.

Referring jointly to FIGS. 2 and 3, further details attendant the needle receiving elements of receptacle 10 will be described. Post 38 attendant recess 30 depends from a segment of supporting surface 36. By incorporating recess 30, anterior end 32 of holder 34 is reasonably well guided and supported during rotation of the holder to prevent skewing of the double ended needle upon partial unthreading and the act of unthreading will be enhanced. Moreover, the recess will maintain the holder in axial alignment with slot 40 to ensure continuing engagement of rib 42 of the hub with the slot. Top surface 49 of post 38 is necessarily dropped below supporting surface 36 to an extent sufficient to accommodate the extending axial dimension of boss 46 and the axial positioning of a band 47 normally found in hub 44, which band segregates the ribbed portion of the hub from the threaded portion of the hub. As noted above, a downward canting of top surface 49 is preferable to encourage sideways movement of a freed double ended needle to assist the hub in clearing the post prior to dropping into receptacle 10. As particularly noted in FIG. 2, post 38 may extend across a chord of aperture 39 defined by supporting surface 36. Such configuration will assist in locating the hub of the needle with respect to slot 40 and minimize the likelihood of the hub missing or not engaging the post in the manner intended.

Passageway 90 includes and is defined by a depending annular skirt 98, which skirt guides and stabilizes collar 78 upon mounting of device 52. A shelf 100 extends centrally into passageway 90 from skirt 98, which shelf supports post 94. The post may include a curved side 102 concentric with passageway 90 to define therebetween an annular slot 104 for receiving a segment of collar 78 of device 50. Slot 92 may extend inwardly from a flat surface 106 interconnecting opposed edges of curved side 102.

As will be evident by inspection, annular slot 104 in combination with the remaining surface area of skirt 98 defining passageway 90 will permit unimpeded rotation of device 50 about its longitudinal axis (and double ended needle 62) but generally impede pivoting or lateral displacement of the device. The limited permissible movement of the device will encourage non binding interference between the rib engaged with slot 9 and permit ready disengagement upon dropping of the double ended needle after threaded disconnection between hub 60 and boss 56.

Figure 4:
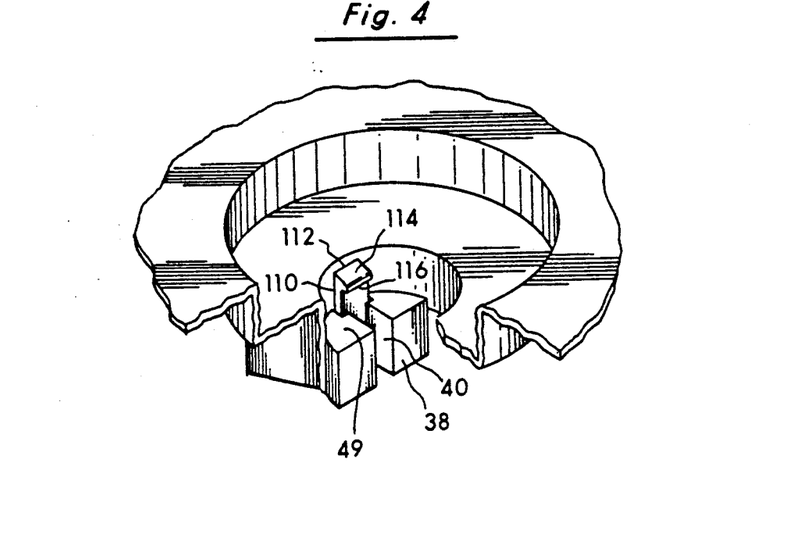
FIG. 4 illustrates a variant of the hub engaging post structure.

Referring to FIG. 4 there is shown a variant structure for either or each of posts 38,94. Under abnormal conditions, a double ended needle may not disengage from the supporting post and drop into receptacle 10 as intended and expected. To encourage lateral movement of the hub of the respective double ended needle off of the top surface of the respective post an to totally eliminate any basis for support for the double ended needle, bias means may be incorporated to force the needle out of engagement with the post. A bias means of this type is illustrated in FIG. 4. A leaf spring 110 is disposed at the rear of a slot, such as slot 40, of one of the posts, such as post 38. This leaf spring may be formed as part of the post with its lower end extending upwardly from the lower part of the post. As illustrated, the leaf spring may replace the wall portion of the post directly rearwardly of the respective slot; the leaf spring may be formed in place of a part of the wall portion depicted in FIGS. 2 and 3; or, the leaf spring may be separate from the post. By having leaf spring 110 extend forwardly in its relaxed state, it will be forced rearwardly upon engagement of a double ended needle hub with the post. Accordingly, the leaf spring will bear against and bias the hub out of the slot. Upon disengagement of the double ended needle from the blood collection tube holder, the double ended needle will no longer be positionally restrained and the bias urged by the leaf spring will be exercised. Such exercise will cause the double ended needle to be urged out of engagement with the slot. Leaf spring 110 thereby contributes to release of the double ended needle to permit it to drop under force of gravity into the underlying receptacle; the drop may be augmented by the leaf spring. As depicted in FIG. 4, top surface 49 may be canted to further encourage disengagement between the double ended needle and the post.

Conventional double ended needles include a band disposed about the hub intermediate the threaded segment and the ribbed segment, as illustrated in FIG. 3. Under certain circumstances, despite threaded disengagement between a blood collection tube holder and a double ended needle, the double ended needle may remain attached to the boss of the blood collection tube holder. Upon withdrawal of the blood collection tube holder, the double ended needle may inadvertently be withdrawn from receptacle 10 and later drop somewhere else. To prevent this from happening, leaf spring 110, as shown in FIG. 4, includes a lip 112 for bearing against the upper edge of the band attendant the hub of the double ended needle. Because of the bias provided by the leaf spring, the lip will be urged toward the hub for such engagement. To permit passage of the band past the lip upon insertion of the double ended needle, a ramp 114 may be formed to force the lip laterally as the band passes therepast. The resulting sharp edge 116 will assist repositioning of the lip adjacent the top edge of the band of the hub upon initial unthreading of the hub. Upon upward movement of the holder due to threaded release of the double ended needle, the lip, bearing against the upper edge of the band about the hub, will then move over the top surface of the band and restrain upward movement of the double ended needle. Such restraint will be enough to completely disengage the needle from the blood collection tube holder. Once complete disengagement is effected and with the aid of the leaf spring mounted lip, the double ended needle is free to drop into the receptacle, as discussed above.

Figure 5:
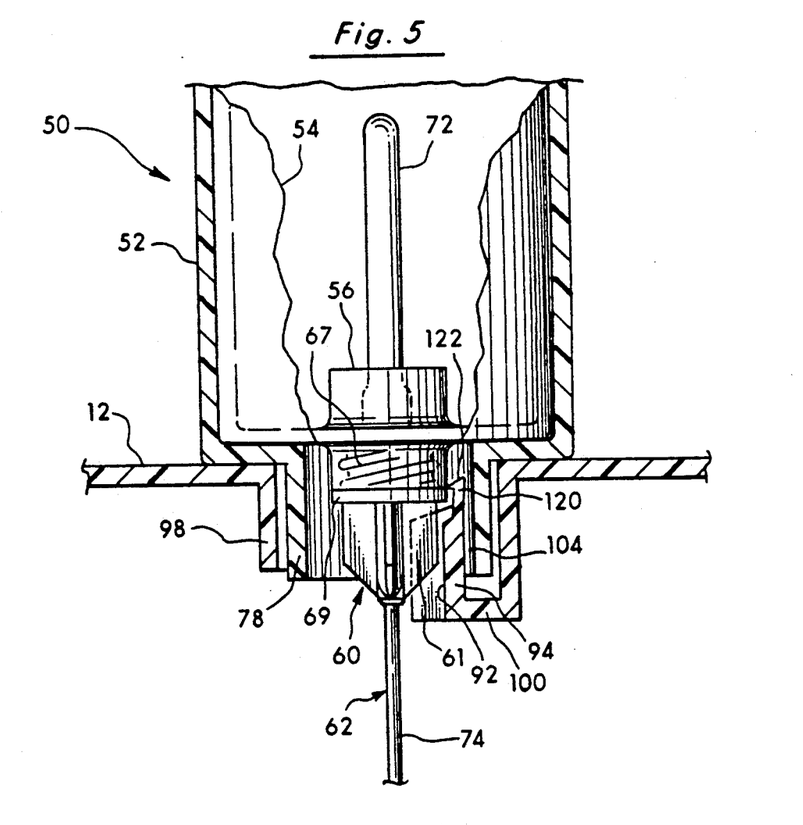
FIG. 5 is a partial cross sectional view illustrating operation of the variant shown in FIG. 4.

A further structural configuration of leaf spring 110 with its lip 122 is depicted in FIG. 5. Post 94, as also shown in FIG. 3, includes a slot 92 for receiving rib 61 of hub 60 in threaded engagement with boss 56 of device 50. The hub includes an annular band 69 disposed intermediate the plurality of ribs and threaded segment 67. Bias means, which may be a leaf spring 120, extends upwardly from post 94 laterally of slot 92. The upper end of the leaf spring includes a lip 122 extending from the leaf spring toward the slot. The vertical position of lip 122 is set to permit band 69 to be placed intermediate the top of post 94 and the lip. Furthermore, the orientation of the leaf spring, in combination with the extent of lip 122, is established to ensure overlap of the lip with the band upon engagement of hub 60 with post 94. Upon such initial engagement, the band may cause the leaf spring to spring rearwardly (laterally) to permit the band to clear the lip. Upon further downward movement of the band, the leaf spring will cause the lip to translate forwardly (laterally) into an overlying engagement with the band. Subsequent upward movement of hub 60 would result in interference between band 69 and lip 122 to discourage further upward movement. Thereby, lip 122 in combination with its supporting leaf spring 120, will encourage complete disengagement between double ended needle 62 and boss 56.

Figure 6:
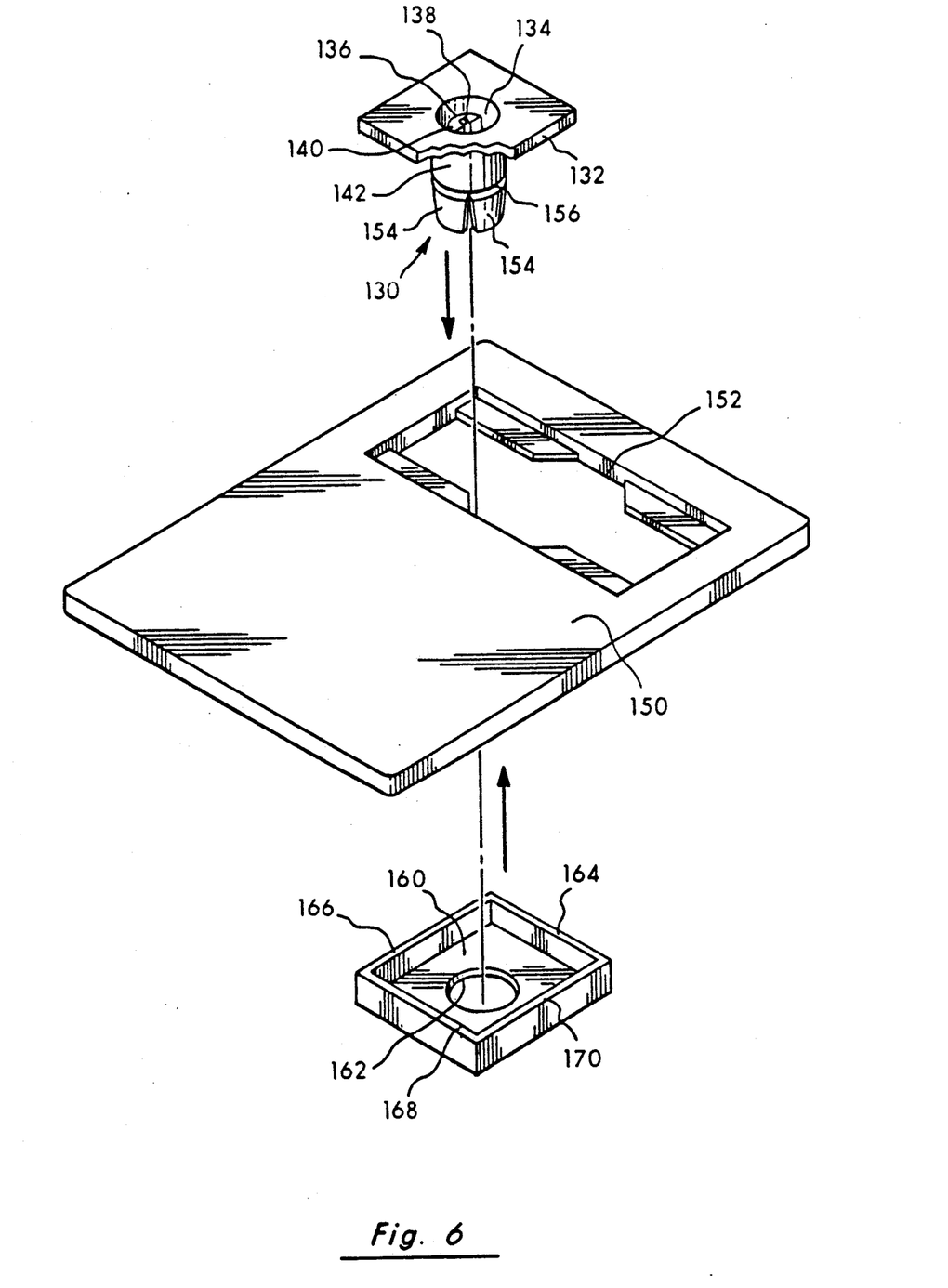
FIG. 6 is an exploded view illustrating a variant of the present invention and mounting means therefor.

FIG. 6 illustrates a variant of the present invention usable in conjunction with any container or receptacle having a lid, which receptacle is to be employed for receiving used double ended needles. A module 130 includes a plate 132 having a recess 134 formed therein; this recess may be of the type shown in FIG. 3 for use with a blood collection tube holder 34 or for use with a blood collection device 50. As described above, a post 136 having a slot 138 is disposed within recess 134. Top surface 140 of post 136 may be horizontal, as depicted, or may be canted, as shown in FIG. 3. A circular shroud 142 extends downwardly from plate 132. This shroud serves in the manner of a guide or chute to direct disengaged double ended needles therethrough.

Module 130 is to be used in conjunction with a receptacle having an apertured top for penetrably receiving shroud 142. Thereby, any receptacle can be used as a disposal unit for double ended needles upon attachment of module 130. The means for retaining the module in place may be permanent or temporary.

A top 150 of a presently widely used receptacle is depicted. The top includes an aperture 152 of sufficient size to permit penetrable engagement by shroud 142. The length and width of plate 132 supports module 130 upon top 150 after penetration of shroud 142. The lower end of the shroud may include a plurality of outwardly biased resilient wings 154 extending downwardly from a groove 156 formed in the shroud. Locking means, such as plate 160, includes an aperture 162 dimensioned to be seated in groove 156.

In operation, module 130 is penetrably engaged with aperture 152 of top 150. Protruding wings 154 are forced radially inwardly to pass through aperture 162 in plate 160 and the plate is translated upwardly along shroud 142 until aperture 162 seats within groove 156. Thereafter, wings 154 will tend to spread radially outwardly to prevent disengagement of plate 160. The module will now be locked in place. Plate 160 may include upwardly extending sidewalls 164, 166, 168 and 170 to provide dimensional correspondence between the extent to which groove 156 is below top 150 with the position of aperture 162 of plate 160 to preclude vertical movement of the module and to frictionally maintain the module at a predetermined location within aperture 152.

Even though top 150 having a particularly configured aperture 152 corresponds with a widely used type of receptacle, it is to be understood that module 130 may be used with any receptacle having an aperture sufficient in size to penetrably receive shroud 142 and permit locking the module in place with a plate, such as plate 160.

Blood collection holder device 50, illustrated in FIGS. 1, 3 and 5, was developed by Medical Safety Products, Inc. for the purpose of eliminating exposure of both the anterior and posterior needles of a double ended needle while handling of the holder other than during the venipuncture procedure itself. That is, after attachment of a conventional double ended needle, the device may be immediately used for venipuncture; alternatively, the double ended needle may be retracted within the guard of the device in the event there will be a time lapse prior to use. After withdrawal of the needle on completion of a venipuncture procedure, the anterior needle is retracted within the guard to prevent needle stick and to contain any body fluids of the patient which may be on or about the needle. Prior to retraction, the posterior needle is shielded by both the holder and the guard. Upon retraction of the double ended needle, the posterior needle remains shielded within the holder to prevent needle stick or contact therewith by a clinician. Passageway 90 of receptacle 10 receives the collar extending anteriorly from the barrel, which collar may partly house and shield the end of the anterior needle. Prior to and during the act of mating the collar with passageway 90, the anterior needle remains shielded and accidental contact therewith by a clinician will be precluded. During extension of the double ended needle prior to segregation of the needle from the holder, the anterior needle is interior of receptacle 10, which receptacle shields the needle against accidental contact by the clinician After unthreading of the double ended needle from the holder, the needle will drop into the receptacle with little possibility that the clinician can contact either the anterior or posterior needle of the double ended needle. Accordingly, the combination of device 50 and receptacle 10 provides apparatus which will completely safeguard a clinician from contact with a double ended needle during the time subsequent to a venipuncture procedure to final disposal of the double ended needle.

Single ended needles attached to hypodermic needles have similar ribbed hubs. Accordingly, the present invention can be used to disengage such needles from their syringes.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A disposal for receiving double ended needles being in engagement with a blood collection tube holder and aligned with the longitudinal axis of the holder, said disposal comprising in combination:
    a) a receptacle for housing the needles;
    b) means disposed in said receptacle for receiving the anterior end of the holder and for accommodating rotation of the holder about its longitudinal axis, which holder includes a boss for engaging a hub disposed upon the double ended needle, said receiving means including means for supporting at least a part of the anterior end of the holder;
    c) a post disposed within said receiving means for engaging the hub to prevent rotation of the hub about the longitudinal axis of the holder;
    d) means for interferingly aligning the hub with said post upon axial movement of the holder along its longitudinal axis to engage the hub with said post and for preventing lateral displacement of the holder from its longitudinal axis; and
    e) an aperture disposed in said receiving means for accommodating passage of the needle upon disengagement of the double ended needle from the holder resulting from rotation of the holder relative to the hub and withdrawal of the holder from said receiving means.

2. The apparatus as set forth in claim 1 wherein the hub includes longitudinally aligned ribs and wherein said engaging means comprises a slot disposed in said post for engaging a rib of the hub.

3. The apparatus as set forth in claim 1 wherein said supporting means includes a segment of an annular surface.

4. The apparatus as set forth in claim 1 including means for urging disengagement of the needle from the holder.

5. The apparatus as set forth in claim 4 wherein said urging means comprises a leaf spring.

6. The apparatus as set forth in claim 5 wherein said leaf spring extends from said post.

7. The apparatus as set forth in claim 5, said leaf spring includes a lip for engaging the hub to prevent rise of the needle upon withdrawal of the holder from said recess.

8. The apparatus as set forth in claim 1 wherein said holder is transparent to permit viewing disengagement of the needle from the holder.

9. The apparatus as set forth in claim 8 wherein said receptacle includes means to permit viewing drop of the needle into said receptacle.

10. A disposal for receiving double ended needles having a ribbed hub threadedly engaged with a blood collection tube holder translatable within a guard having a collar disposed at the anterior end for receiving the hub, said disposal comprising in combination:
    a) a receptacle for housing the needles;
    b) a passageway in communication with the interior of said receptacle for receiving the collar of the guard;
    c) means for supporting the anterior end of the guard upon placement of the collar within said passageway;
    d) a post disposed within said passageway, said post including means for engaging a rib of the ribbed hub to prevent rotation of the hub about the longitudinal axis of the needle; and
    e) means for accommodating passage of the needle into said receptacle upon threaded disengagement of the needle from the holder resulting from rotation of the guard relative to the hub and withdrawal of the collar from said passageway.

11. The apparatus as set forth in claim 10 wherein said engaging means comprises a slot disposed in said post for engaging a rib of the ribbed hub.

12. The apparatus as set forth in claim 10 including means for urging disengagement between said post and the threadedly disengaged needle.

13. The apparatus as set forth in claim 12 wherein said urging means comprises a leaf spring.

14. The apparatus as set forth in claim 13 wherein said leaf spring extends from said post.

15. The apparatus as set forth in claim 13 wherein said leaf spring includes a lip for engaging the hub to prevent rise of the needle upon withdrawal of the holder from said recess.

16. The apparatus as set forth in claim 10 wherein said supporting means comprises said top.

17. The apparatus as set forth in claim 10 including a skirt depending from said top for defining said passageway.

18. The apparatus as set forth in claim 17 including a shelf extending from said skirt for supporting said post.

19. The apparatus as set forth in claim 18 including a segment of an annular slot disposed between said post and said skirt for receiving the collar.

20. The apparatus as set forth in claim 10 wherein said holder is transparent to permit viewing disengagement of the double ended needle from the holder.

21. The apparatus as set forth in claim 10 wherein said receptacle includes means to permit viewing drop of the needle into the receptacle.

22. A method for disposing a double ended needle detachably attached to a blood collection tube holder, said method comprising the steps of:
    a) providing a receptacle for housing the needles;
    b) receiving the anterior end of the holder in a recess disposed in the receptacle, which recess accommodates rotation of the holder about its longitudinal axis and supports at least a part of the anterior end of the holder, the holder including a boss for threadedly engaging a ribbed hub disposed upon the needle;
    c) engaging rib of the ribbed hub with a post disposed in the recess to prevent rotation of the hub about the longitudinal axis of the needle upon axial movement of the holder along its longitudinal axis;
    d) preventing lateral displacement of the holder from its longitudinal axis during said step of engaging; and
    e) passing the needle through an aperture disposed in the recess and into the receptacle upon a threaded disengagement of the needle from the holder resulting from rotation of the holder relative to the hub and subsequent withdrawal of the holder.

23. The method as set forth in claim 22 including the step of urging disengagement of the needle with the post upon threaded disengagement of the needle from the holder.

24. The method as set forth in claim 23 including the step of restraining rise of the needle commensurate with withdrawal of the holder.

25. A method for disposing double ended needles having a ribbed hub threadedly engaged with a blood collection tube holder translatable within a guard having a collar disposed at the anterior end for receiving the hub, said method comprising the steps of:
    a) providing a receptacle for housing the needles;
    b) receiving the collar of the guard in a passageway in communication with the interior of the receptacle;
    c) supporting the anterior end of the guard upon placement of the collar within the passageway;
    d) engaging a rib of the ribbed hub with a post disposed in the passageway to prevent rotation of the hub about the longitudinal axis of the needle; and
    e) passing the needle through the passageway and into the receptacle upon threaded disengagement of the needle from the holder resulting from rotation of the holder relative to the hub and withdrawal of the holder.

26. The method as set forth in claim 25 including the step of urging disengagement of the needle with the post upon threaded disengagement of the needle from the holder.

27. The method as set forth in claim 26 including the step of restraining rise of the needle commensurate with withdrawal of the holder.

28. A method for disposing a used conventional double ended needle detachably attached to a blood collection tube holder, said method comprising the steps of:
    a) housing the used needle within a receptacle;
    b) stabilizing and supporting the anterior end of the holder to accommodate rotation of the holder about its longitudinal axis, which holder includes a boss for threadedly engaging a ribbed hub disposed upon the needle;

c) engaging the ribbed hub to prevent rotation of the hub about the longitudinal axis of the needle;
d) preventing lateral displacement of the holder from its longitudinal axis during said step of engaging; and
e) accommodating passage of the needle into the receptacle upon threaded disengagement of the needle from the holder resulting from rotation of the holder relative to the hub.

29. The method as set forth in claim 28 including the step of urging passage of the needle into the receptacle.

30. A disposal for receiving used conventional double ended needles being in threaded engagement with a blood collection tube holder and aligned with the longitudinal axis of the holder, said disposal comprising in combination:
a) means for housing the used needles;
b) means for stabilizing and supporting the anterior end of a blood collection tube holder and for accommodating rotation of the holder about its longitudinal axis while precluding lateral movement of the holder, the anterior end of the holder including a boss for threadedly engaging a ribbed hub disposed upon the double ended needle;
c) means for engaging the ribbed hub to prevent rotation of the hub about the longitudinal axis of the holder; and
d) said stabilizing, supporting and accommodating means including means for aligning the hub with said engaging means upon axial movement of the holder along its longitudinal axis to engage the hub with said engaging means and for preventing lateral displacement of the holder from its longitudinal axis; and
e) means for accommodating passage of the needle into said housing means upon threaded disengagement of the needle from the holder resulting from rotation of the holder relative to the hub.

31. The apparatus as set forth in claim 30 wherein said engaging means comprises a slot for receiving a rib of the ribbed hub.

32. The apparatus as set forth in claim 30 wherein said stabilizing, supporting accommodating means comprises a recess for receiving the anterior end of the holder.

33. The apparatus as set forth in claim 32 wherein said engaging means is disposed within said recess.

34. The apparatus as set forth in claim 30 wherein said stabilized and supporting means includes a cylindrical skirt extending into said housing means.

35. The apparatus as set forth in claim 34 wherein said engaging means is disposed within said skirt.

36. The apparatus as set forth in claim 30 including means for urging disengagement between said engaging means and the needle.

37. A disposal for receiving used conventional single ended needles used with a conventional hypodermic syringe and having a ribbed hub for engaging a boss of the hypodermic syringe, said disposal comprising in combination:
a) means for housing the used needles;
b) means for stabilizing and supporting the anterior end of the hypodermic syringe to accommodate rotation of the hypodermic syringe about its longitudinal axis while precluding lateral movement thereof;
c) means for engaging the ribbed hub of the needle to prevent rotation of the hub about the longitudinal axis of the needle; and
d) means for accommodating passage of the needle into said housing means upon threaded disengagement of the needle from the hypodermic syringe resulting from rotation of the hypodermic syringe relative to the hub.

38. The apparatus as set forth in claim 37 wherein said engaging means comprises a slot for receiving a rib of the ribbed hub.

39. The apparatus as set forth in claim 37 wherein said stabilizing and supporting means comprises a recess for receiving the anterior end of the hypodermic syringe.

40. The apparatus as set forth in claim 39 wherein said engaging means is disposed within said recess.

41. The apparatus as set forth in claim 37 wherein said stabilized and supporting means includes a cylindrical skirt extending into said housing means.

42. The apparatus as set forth in claim 41 wherein said engaging means is disposed within said skirt.

43. The apparatus as set forth ian claim 37 including means for urging disengagement between said engaging means and the needle.

44. A disposal for receiving each of a plurality of double ended needles detachably attached to a blood collection tube holder having a longitudinal axis, said disposal comprising in combination:
a) a receptacle for housing the needles;
b) means for supporting at least a part of the anterior end of the holder, which holder includes a boss for threadedly engaging a ribbed hub disposed upon the double ended needle;
c) a post, said post including means for engaging a rib of the ribbed hub to prevent rotation of the hub about the longitudinal axis of the double ended needle in response to rotation of the holder;
d) means for interferingly aligning the hub with said post upon axial movement of the holder along its longitudinal axis to engage the hub with said post and for preventing lateral displacement of the holder from its longitudinal axis; and
e) an aperture for accommodating passage of the double ended needle into said receptacle upon threaded disengagement of the double ended needle from the holder resulting from rotation of the holder relative to the hub.

45. A disposal for receiving double ended needles having a ribbed hub threadedly engaged with a blood collection tube holder translatable within a guard having a collar disposed at the anterior end for receiving and encircling the hub to define an annular space about the ribbed hub, said disposal comprising in combination:
a) a receptacle for housing the needles;
b) means for supporting the anterior end of the guard relative to said receptacle;
c) a post associated with the receptacle for extending into the annular space defined by the collar, said post including means for engaging a rib of the ribbed hub to prevent rotation of the hub about the longitudinal axis of the needle; and
d) means for accommodating passage of the needle into said receptacle upon threaded disengagement of the needle from the holder resulting from rotation of the guard relative to the hub and withdrawal of the guard from a supported relationship with said receptacle.

* * * * *